United States Patent [19]

Berges et al.

[11] 4,308,267

[45] Dec. 29, 1981

[54] 7-[2-ALKOXYIMINO-2-(AMINO-THIAZOLE)ACETAMIDO]-3-[1-(SULFAMINOALKYL)TETRAZOLTHIOMETHYL]CEPHALOSPORINS

[75] Inventors: David A. Berges, Phoenixville; George L. Dunn, Wayne, both of Pa.

[73] Assignee: SmithKline Corporation, Philadelphia, Pa.

[21] Appl. No.: 165,822

[22] Filed: Jul. 3, 1980

[51] Int. Cl.³ ................. C07D 501/56; A61K 31/545
[52] U.S. Cl. .................................... 424/246; 544/21; 544/27
[58] Field of Search ..................... 544/27, 21; 424/246

[56] References Cited

U.S. PATENT DOCUMENTS 4,066,762  1/1978  Dunn .
4,152,432  5/1979  Heymes et al. .
4,171,362  10/1979  Berges .................................... 544/27
4,220,761  9/1980  Takaya et al. ...................... 424/246

FOREIGN PATENT DOCUMENTS 853545   10/1977  Belgium .
865632   10/1978  Belgium .
2922036  5/1979   Fed. Rep. of Germany .

*Primary Examiner*—Paul M. Coughlan, Jr.
*Attorney, Agent, or Firm*—Stuart R. Suter; Alan D. Lourie; Richard D. Foggio

[57] ABSTRACT

Novel cephalosporins with improved antibacterial and pharmacokinetic properties are disclosed. These compounds have a 2-alkoxyimino-2-(2-amino-4-thiazolyl)-acetamido group at position 7 and a sulfaminoalkyltetrazolythio group at position 3.

8 Claims, No Drawings

7-[2-ALKOXYIMINO-2-(AMINO-THIAZOLE)ACETAMIDO]-3-[1-(SULFAMINOALKYL)TETRAZOLTHIOMETHYL]-CEPHALOSPORINS

BRIEF DESCRIPTION OF THE INVENTION

This invention comprises new cephalosporin compounds which have antibacterial activity. The invention also comprises pharmaceutical compositions of the novel compounds and methods of treating bacterial infections in animals. The compounds of this invention are characterized by having an 2-(aminothiazolyl)-2-(alkoxyimino)-acetamido group at position 7 and at position 3 a tetrazolylthiomethyl group which is substituted with a sulfaminoalkyl moiety.

The compounds of this invention exhibit potent antibacterial activity against a broad range of Gram-positive and Gram-negative bacteria. In addition, the compounds of the invention exhibit improved pharmacokinetic properties.

PRIOR ART STATEMENT

Cephalosporin compounds with various 2-oximinoacetamido substituents at position 7 have been disclosed in the prior art. United States Patent No. 4,066,762 discloses cephalosporins with the furyloximinoacetamido group including the 2-(2-furyl)-2-methoxyiminoacetamido substituent and the tetrazolylthiomethyl substituent. The tetrazole moiety was substituted with a sulfoalkyl (alk—$SO_3H$), sulfamylalkyl (alk—$SO_2NH_2$), sulfaminoalkyl (alk—$NHSO_3H$) or methylsulfamidoalkyl (alk—$NHSO_2CH_3$) group.

The 2-(2-amino-4-thiazolyl)-2-syn-methoxyiminoacetamido group is disclosed as a substituent on cephalosporins in the prior art. U.S. Pat. No. 4,152,432 discloses the compound 7-[2-(2-amino-4-thiazolyl)-2-methoxyiminoacetamidocephalosporanic acid. Compounds with the same acyl group and a substituted tetrazolylthiomethyl group at position 3 are disclosed in Belgian Pat. No. 865,632 and 853,545. Within these patents 7-[2-(2-amino-4-thiazolyl)-2-methoxyiminoacetamido]-3-(1-sulfomethyltetrazol-5-ylthiomethyl)-3-cephem-4-carboxylic acid is disclosed.

DESCRIPTION OF THE INVENTION

The compounds of this invention are represented by the following structural formula:

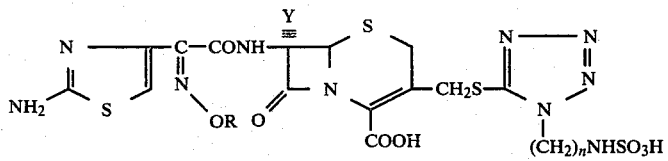

wherein:
R is hydrogen or lower alkyl of 1-4 carbon atoms,
Y is hydrogen or methoxy, and
n is 2 to 5.

Preferred compounds are those where R is methyl and n is two. The structural formula shown above intends to show the isomeric configuration of the oximino group to by syn or z configuration. Although the syn isomers are preferred and show the best biological properties, they may coexist with small amounts of the anti-isomer which may exist due to isomerization during the chemical preparation.

Also included within the scope of this invention are hydrates and pharmaceutically acceptable salts of the novel cephalosporin compounds. The compounds may exist in solutions as the zwitterion but are more stable in the salt form. Therefore the compounds are preferably isolated as a salt. Both acid or base salts are readily prepared by well-known standard methods.

Due to the two acidic moieties present in the compounds, mono or di salts or mixtures of the two may exist. Many examples of pharmaceutically acceptable salts are known in the art including alkali metal salts such as sodium or potassium salts, the alkaline earth salts such as calcium salts, ammonium salts and organic amine salts such as procaine or dibenzylethylenediamine salts. In addition, acid addition salts of the amine group are also possible and within the scope of this invention. Such salts are formed from both inorganic and organic acids, such as maleic, fumaric, benzoic, ascorbic, pamoic, succinic, 5,5'-methylenedisalicyclic, methanesulfonic, ethanedisulfonic, acetic, oxalic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric, and nitric acids. The salts may also exist in hydrated form.

The compounds of this invention are prepared by known methods whereby the acetoxy group of the cephalosporin compound of Formula I is displaced with the appropriate sulfaminoalkyltetrazolylmercaptan of Formula II.

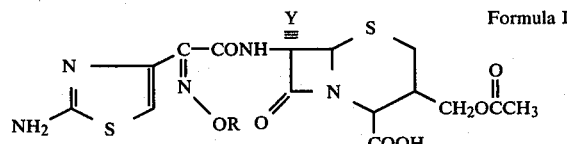

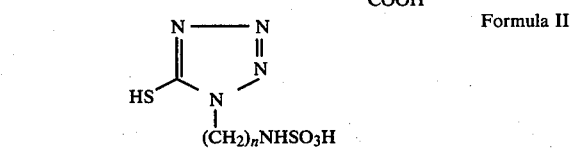

Within Formulae I and II R, Y, and n are as described above. The displacement of the acetoxy group is well known in the art and process conditions which use a buffered aqueous solution or an organic solvent system are documented; see, for example, Flynn, ed. Cephalosporins and Penicillins—Chemistry and Biology, Academic Press, New York, 1972 and U.S. Pat. Nos. 3,278,531 and 4,144,391.

Alternatively the compounds of this invention are prepared by known methods whereby the appropriate 7-amino cephem nucleus of Formula III is acylated with a compound of Formula IV or a derivative of such compound.

TABLE I

| | 1 | 2 | 3 | 4 | 5 | 6 | 7 | 8 | 9 |
|---|---|---|---|---|---|---|---|---|---|
| | \multicolumn{9}{c}{MINIMUM INHIBITORY CONCENTRATION (μg/ml)} |
| | Staph. aureus* HH 127 | Staph. aureus* 671 | Staph. aureus 674 | Strep. faecalis HH 34358 | E. coli SK&F 12140 | E. coli* 804 | Kleb. pneumoniae SK&F 4200 | Kleb. pneumoniae SK&F 1200 | Kleb. pneumoniae* 982 |
| Compound A | 6.3 | 3.1 | 6.3 | >100 | ≦0.1 | 0.4 | ≦0.1 | ≦0.1 | 1.6 |
| Cefamandole | 1.6 | 6.3 | ≦0.1 | 25 | 0.8 | >100 | 1.6 | 0.4 | >100 |
| Cefatoxime | 1.6 | 0.4 | 0.8 | >100 | ≦0.1 | 0.2 | ≦0.1 | ≦0.1 | 0.2 |

| | 10 | 11 | 12 | 13 | 14 | 15 | 16 |
|---|---|---|---|---|---|---|---|
| | \multicolumn{7}{c}{MINIMUM INHIBITORY CONCENTRATION (μg/ml)} |
| | P. mirabilis PM-444 | Pseudo. aeruginosa HH 63 | Serratia marcescens ATCC 13880 | Proteus morgani 179 | Enterobacter aerogenes ATCC 13048 | Enterobacter cloacae 921 | Pseudo. aeruginosa 647 |
| Compound A | ≦0.1 | 12.5 | ≦0.1 | ≦0.1 | 0.2 | 0.2 | 6.3 |
| Cefamandole | 0.4 | >100 | 12.5 | 1.6 | 1.6 | 3.1 | >100 |
| Cefatoxime | ≦0.1 | 6.3 | ≦0.1 | ≦0.1 | ≦0.1 | ≦0.1 | 3.1 |

*β-lactamase producer

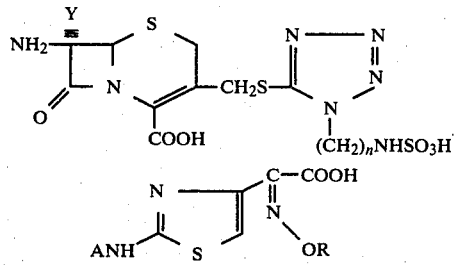

Formula III

Formula IV

Within Formulae III and IV R, Y, and n are as described above and A is an amino protecting group. The acylation reaction is carried out by standard methods. The carboxylic acid group is activated by normal methods such as conversion to a mixed anhydride, acid chloride or an activated ester.

The starting materials of Formulae I to IV are known in the art or are prepared by known methods. U.S. Pat. Nos. 4,118,491 and 4,152,432 teach methods to prepare these starting materials.

During the reactions described above it may be necessary or advantageous to use a protecting group for the amino, hydroxyl or carboxylic moieties. Many groups useful for this purpose are known and used in the art. Furthermore, the proper selection and appropriate use of the protecting group is easily done by a person skilled in the art.

The compounds of this invention are useful as broad spectrum antibacterial agents against both Gram-positive and Gram-negative organisms. The compound 7-[syn-2-methoxyimino-2-(2-amino-4-thiazolyl)acetamido]-3-[1-(2-sulfaminoethyl)tetrazo-5-ylthiomethyl]-3-cephem-4-carboxylic acid disodium salt (Compound A) exhibits high activity in standard in vitro screens, especially against Gram-negative bacteria including those which are β-lactamase producers. Minimum inhibitory concentrations (MIC) of Compound A and a commercial cephalosporin agent cefamandole are shown in Table 1. Data for 7-[syn-2-methoxyimino-2-(2-amino-4-thiazolyl)acetamido]cephalosporanic acid (cefatoxime) are also included for comparison.

Compound A also exhibits high antibacterial activity in standard in vivo tests in mice. Table 2 sets forth $ED_{50}$'s for Compound A, cefamandole and cefatoxime.

In addition, Compound A exhibited unexpected improved pharmacokinetic properties. For example, peak serum levels, serum levels at two hours and half-life were better for Compound A compared to cefatoxime and cefamandole. The results are tabulated in Table 3.

TABLE 2

| | $ED_{50}$ (mg/kg) | |
|---|---|---|
| | S. aureus HH 127 | E. coli 12140 |
| Compound A | 21 | 0.4 |
| Cefamandole | 2.2* | 0.9* |
| Cefatoxime | 10.5 | <0.2 |

*representative value

TABLE 3

| Mouse (20 mg/kg) | Compound A | Cefatoxime | Cefamandole |
|---|---|---|---|
| Peak Serum Level (μg/ml) | 78 | 25 | 34 |
| Serum Level at 2 hrs. (μg/ml) | 52 | <1 | 1 |
| Half-life (Minutes) | 114 | 27 | 12 |
| Urinary Recovery (%) | 24 | 13 | 45 |
| Binding to Human Serum Proteins (%) | 70 | 39 | 61 |

The compounds of this invention are formulated into pharmaceutical compositions by methods known in the cephalosporin art. The compositions are administered internally to subjects to prevent or cure bacterial infections. Injectable compositions are preferred which are administered by the parenteral route. Daily dosages are from 1-8 g. which are administered in 1-5 divided dosages.

The following examples are presented to illustrate to persons skilled in the art methods of preparation and use of the compounds of this invention.

EXAMPLE 1

7β-[syn-2-methoxyimino-2-(2-amino-4-thiazolyl)acetamido]-3-[1-(2-sulfaminoethyl)tetrazol-5-ylthiomethyl]-3-cephem-4-carboxylic acid A solution of 7-[syn-2-methoxyimino-2-(2-amino-4-thiazolyl)acetamido]cephalosporanic acid (2.3 g., 5 mmol.) and 1-(2-sulfaminoethyl)tetrazol-5-thiol disodium salt (1.25 g., 4.6 mmol.) in water (30 ml.) containing NaHCO₃ (0.4 g.) was heated with stirring at 65° for 4.5 hours. The reaction mixture was concentrated to half volume and adjusted to pH 6.8 with solid NaHCO₃. The resulting mixture was chromatographed on nonionic polymer resin 'XAD-7' (Rohm and Haas) column bed (2"×20") with water as eluant. Fractions (20 ml.) were collected after UV absorbing material was detected. Unreacted thiol was eluted followed by the titled product. The fractions containing product were concentrated in vacuo to a small volume and then freeze-dried to give product (1.15 g.). This material was dissolved in water (8 ml.) and chromatographed on a 'BioGel-P-2' (Bio-Rad Laboratories) column (2"×42" bed) with distilled water as eluant at a 13 ml. per 3 minute flow rate. Fractions with product were identified by tlc (silica gel; 70:30:3 methylene chloride: methanol:formic acid), combined, concentrated to a small volume and freeze dried to give the disodium salt of the title product (940 mg., 31.2%).

Improved yields are obtained when the displacement reaction described above is run with 50% excess of the tetrazolethiol disodium salt. The excess thiol is removed by chromatography methods. After the 'XAD-7' column the product is 85-90% pure. Further chromatography on a strong base anion exchange resin of the styrene-divinylbenzene type with 10 to 16 percent cross-linking prior to the 'Bio-Rad-P-2' column gives a product of about 95% purity.

EXAMPLE 2

Substitution of 1-(3-sulfaminopropyl)tetrazol-5-thiol or 1-(5-sulfaminopentyl)tetrazol-5-thiol for the thiol in Example 1 gives the following products as their disodium salt:

7β-[syn-2-methoxyimino-2-(2-amino-4-thiazolyl)-acetamido]-3-[1-(3-sulfaminopropyl)tetrazol-5-ylthiomethyl]-3-cephem-4-carboxylic acid;

7β-[syn-2-methoxyimino-2-(2-amino-4-thiazolyl)-acetamido]-3-[1-(5-sulfaminopentyl)tetrazol-5-ylthiomethyl]-3-cephem-4-carboxylic acid.

EXAMPLE 3

When 7β-[syn-2-methoxyimino-2-(2-amino-4-thiazolyl)acetamido]-7α-methoxycephalosporanic acid is reacted with 1-(2-sulfaminoethyl)tetrazol-5-thiol according to the procedure of Example 1, 7β-[syn-2-methoxyimino-2-(2-amino-4-thiazolyl)acetamido]-7α-methoxy-3-[1-(2-sulfaminoethyl)tetrazol-5-ylthiomethyl]-3-cephem-4-carboxylic acid disodium salt is obtained.

Similarly, when 1-(3-sulfaminopropyl)tetrazol-5-thiol and 1-(5-sulfaminopentyl)tetrazol-5-thiol is reacted with the above-noted cephalosporanic acid derivative the following products are obtained:

7β-[syn-2-methoxyimino-2-(2-amino-4-thiazolyl)acetamido]-7α-methoxy-3-[1-(3-sulfaminopropyl)tetrazol-5-ylthiomethyl]-3-cephem-4-carboxylic acid disodium salt;

7β-[syn-2-methoxyimino-2-(2-amino-4-thiazolyl)-acetamido]-7α-methoxy-3-[1-(5-sulfaminopentyl)tetrazol-5-ylthiomethyl]-3-cephem-4-carboxylic acid disodium salt.

EXAMPLE 4

A parenteral pharmaceutical composition is prepared by dissolving any of the products of this invention in sterile saline solution. For example, an injectable dosage of the product of Example 1 is prepared by dissolving 1 g. of product in 2 ml. of sterile saline solution.

What is claimed is:

1. A compound of the formula

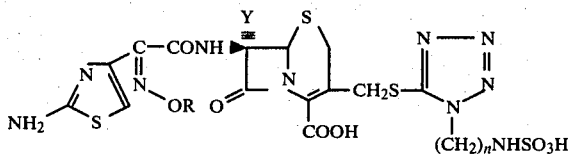

in which
R is hydrogen or lower alkyl of 1-4 carbon atoms,
Y is hydrogen or methoxy,
n is 2-5 or a pharmaceutically acceptable salt thereof.

2. A compound according to claim 1 in which R is methyl.

3. A compound according to claim 2 in which Y is hydrogen.

4. A compound according to claim 3 in which n is 2.

5. The compound according to claim 4 which is 7β-[syn-2-methoxyimino-2-(2-amino-4-thiazolyl)acetamido]-3-[1-(2-sulfaminoethyl)tetrazol-5-ylthiomethyl]-3-cephem-4-carboxylic acid in the zwitterion form.

6. The compound according to claim 5 in the form of its disodium salt.

7. A pharmaceutical composition having antibacterial activity comprising a pharmaceutical carrier and an amount sufficient to produce said activity of a compound of claim 1, 4, 5 or 6.

8. A method of treating bacterial infections which comprises administering internally to an infected or susceptible animal or human subject an antibacterially effective amount of a compound of claim 1, 4, 5 or 6.